(12) United States Patent
Model

(10) Patent No.: US 10,682,114 B2
(45) Date of Patent: Jun. 16, 2020

(54) COMPUTED TOMOGRAPHY SYSTEM AND PATIENT TABLE COMPRISING A CONTACTLESS TRANSFER OF ELECTRICAL SIGNALS

(71) Applicant: SIEMENS HEALTHCARE GMBH, Erlangen (DE)

(72) Inventor: Volker Model, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 231 days.

(21) Appl. No.: 15/301,399

(22) PCT Filed: Feb. 16, 2015

(86) PCT No.: PCT/EP2015/053186
§ 371 (c)(1),
(2) Date: Oct. 2, 2016

(87) PCT Pub. No.: WO2015/149983
PCT Pub. Date: Oct. 8, 2015

(65) Prior Publication Data
US 2017/0105697 A1 Apr. 20, 2017

(30) Foreign Application Priority Data

Apr. 2, 2014 (DE) .................. 10 2014 206 295

(51) Int. Cl.
*A61B 6/00* (2006.01)
*A61B 6/03* (2006.01)
*A61B 6/04* (2006.01)

(52) U.S. Cl.
CPC .............. *A61B 6/56* (2013.01); *A61B 6/032* (2013.01); *A61B 6/035* (2013.01); *A61B 6/0407* (2013.01); *A61B 6/4435* (2013.01)

(58) Field of Classification Search
CPC .................. A61B 6/0407; A61B 6/56
See application file for complete search history.

(56) References Cited

U.S. PATENT DOCUMENTS 3,701,003 A * 10/1972 Anderson ............... H01F 38/30
323/358
4,899,113 A * 2/1990 Buikema ................. H02M 3/28
315/209 R (Continued)

FOREIGN PATENT DOCUMENTS

CA 2239642 A1 12/1998
CN 1130836 A 9/1996

(Continued)

OTHER PUBLICATIONS

German office Action for related German Application No. 10 2014 206 295.0 dated Jan. 15, 2015.

(Continued)

*Primary Examiner* — Dani Fox
(74) *Attorney, Agent, or Firm* — Lempia Summerfield Katz LLC

(57) ABSTRACT

The invention relates to a computer tomography installation having contactless data signal transmission. The device comprises at least one longitudinally slit coaxial conductor element (1), at least one high-frequency transmitting unit (3), which feeds into the conductor element (1) a high-frequency carrier signal modulated with a data signal to be transmitted, at least one longitudinally slit coaxial coupling conductor element (2), which is designed to receive the emitted modulated high-frequency carrier signal (21) from the near field of the conductor element (1), and at least one high-frequency receiving unit (4), which is electrically connected to the coupling conductor element (2) and is designed to extract the data signal from the received modulated high-frequency carrier signal, wherein the conductor ele- (Continued)

ment (1) and the coupling conductor element (2) are arranged in such a way that the conductor element and the coupling conductor element can be moved in relation to each other. The conductor element (1) is arranged on a rotatable gantry part (12), and the coupling conductor element is arranged on a stationary gantry part (13). The invention further relates to a patient table having such data transmission between moving parts.

22 Claims, 4 Drawing Sheets

(56) References Cited

U.S. PATENT DOCUMENTS

| | | | |
|---|---|---|---|
| 5,140,696 | A | 8/1992 | Fox |
| 5,530,424 | A | 6/1996 | Harrison et al. |
| 5,530,425 | A | 6/1996 | Harrison |
| 7,212,077 | B2 | 5/2007 | Schilling et al. |
| 7,248,641 | B2 | 7/2007 | Schilling |
| 7,957,786 | B2 | 6/2011 | Katcha et al. |
| 2005/0040917 | A1 | 2/2005 | Schilling et al. |
| 2007/0035883 | A1* | 2/2007 | Katcha ............... A61B 6/56 360/281.8 |
| 2012/0082294 | A1* | 4/2012 | Virshup ............... A61B 6/405 378/62 |

FOREIGN PATENT DOCUMENTS

| | | |
|---|---|---|
| CN | 1915173 A | 2/2007 |
| DE | 19533819 A1 | 3/1996 |
| DE | 19533821 A1 | 3/1996 |
| DE | 19828605 A1 | 1/1999 |
| DE | 10206160 A1 | 8/2003 |
| DE | 102006036420 A1 | 3/2007 |
| DE | 10245589 B4 | 4/2007 |
| GB | 2328083 B | 1/2002 |

OTHER PUBLICATIONS

PCT International Search Report and Written Opinion of the International Searching Authority dated May 29, 2015 for corresponding PCT/EP2015/053186.

Chinese Office Action for Chinese Application No. 201580017565.3 dated Apr. 1, 2019.

Rampalli, Sitaram et al. "Recent advances in the designs of radiating (leaky) coaxial cables" Proceedings of 40th International Wire and Cable Symposium, pp. 66-77, 1991.

Johnson, Richard C. et al. "Antenna Engineering Handbook" 3rd Edition, Chapter 10, Georgia Institute of Technology. ISSN 1063-665X, ISBN 0-07-032381-X, 1993. pp. 1-61.

Notification under Rule 71 (3) EPU for European Application No. 15 706 728.1-1122 dated Apr. 2, 2020.

* cited by examiner

COMPUTED TOMOGRAPHY SYSTEM AND PATIENT TABLE COMPRISING A CONTACTLESS TRANSFER OF ELECTRICAL SIGNALS

This application is the National Stage of International Application No. PCT/EP2015/0531816, filed Feb. 16, 2015, which claims the benefit of German Patent Application No. 10 2014 206 295.0, filed Apr. 2,2014. The entire contents of these documents are hereby incorporated herein by reference.

FIELD

The present embodiments relates to a computed tomography system and a patient table with a contactless transfer of electrical signals between units that are movable relative to one another.

BACKGROUND

In many medical engineering applications, electrical signals or data is to be transferred from a moving medical engineering system part to a medical engineering system part at rest, and vice versa.

A field of application of the present embodiments relates to the data transfer between the rotating part and the stationary part of a computed tomography system. During operation of the computed tomography system, the data acquired by the x-ray detectors is to be transferred from the rotating part to the stationary part of the computed tomography system in order to be processed further at the stationary part. Large amounts of data is to be transferred within a short period of time.

Many currently available computed tomography systems use a contactless "slip ring" system for data transfer, as is known from, for example, U.S. Pat. No. 5,140,696 A. The data transfer system described therein includes a transmission unit at the rotating part and a reception unit at the stationary part. The transmission unit has at least one radiofrequency line connected to a transmitter as a transmission antenna, which is arranged at the circumference of the rotating part of a rotating frame. The reception unit includes a receiver and at least one reception antenna connected to the receiver. The reception antenna is formed by a short portion of a radiofrequency line. During operation of the computed tomography system, the transmission antenna moves past the reception antenna at a short distance therefrom. The reception antenna is fastened to the stationary part. The signals propagating on the transmitting radiofrequency line couple into the reception antenna via the near field.

DE 102 06 160 A1 discloses such a signal transfer between moving parts, wherein the radiofrequency line is embodied as a strip line with a dielectric.

SUMMARY

The scope of the present invention is defined solely by the appended claims and is not affected to any degree by the statements within its summary.

The present embodiments may obviate one or more of the drawbacks or limitations in the related art. For example, a computed tomography system and a patient table, that enable an electrical data transfer with a high data transfer capacity and little far field interference are provided.

According to one or more pf the present embodiments, a contactless signal transfer is carried out between parts of a computed tomography system or of a patient table, which move relative to one another, via longitudinally slit coaxial conductor elements (e.g., coaxial conductors). The data signal to be transferred is modulated onto a radiofrequency carrier. The contactless transfer then takes place on a narrowband (e.g., modulation bandwidth up to approximately 30% of the radiofrequency carrier frequency) by means of the conduction coupler structure with the longitudinally slit coaxial build. The transfer function of the coupler structure is broadband with a corresponding frequency response (e.g., high-pass behavior). A coaxial line (e.g., the transmission coupler) covers the whole displacement range (e.g., the circle circumference in the case of rotating parts). A second short coaxial line (e.g., the reception coupler) decouples the modulated radiofrequency carrier signal over the length thereof. The length of the coupling path is determined by the carrier frequency and the modulation bandwidth.

One or more of the present embodiments provide a computed tomography system with a contactless data signal transfer including at least one longitudinally slit coaxial conductor element. The computed tomography system also includes at least one radiofrequency transmission unit that feeds a radiofrequency carrier signal, modulated with a data signal to be transferred, into the conductor element, at least one longitudinally slit coaxial coupling conductor element that is embodied to receive an emitted modulated radiofrequency carrier signal from a near field of the conductor element, and at least one radiofrequency reception unit that is electrically connected to the coupling conductor element and configured to extract the data signal from the received modulated radiofrequency carrier signal. The coaxial conductor element is arranged on a rotating or stationary gantry part and the coupling conductor element is correspondingly arranged on the stationary or rotating gantry part.

On account of the structural properties of the longitudinally slit coaxial lines, one or more of the present embodiments provide an excellent behavior with respect to the far-field damping, leading to a high stability and a very low emission of the modulated signal. The data transfer is suitable, for example, for transfer in the single-digit and two-digit gigahertz range. The conduction coupler may be implemented in a cost-effective manner from a coaxial line by partial skinning or by an insulated inner conductor, embedded in a groove, with a defined wave impedance.

In a development, the frequency of the radiofrequency carrier signal may be greater than 10 GHz. In one embodiment, a transfer may be carried out in the K and Ka band between 18 and 35 GHz. Higher frequencies up to 60 GHz may be provided, but lead to reduction in the coaxial cross section.

In a further embodiment, the device includes a first carrier element, in which the coaxial conductor element is formed.

In a further embodiment, the first carrier element may be made of metal and forms a first outer conductor of the coaxial conductor element. The cross section of the first carrier element may be rectangular, and a first inner conductor is arranged in a groove of the first carrier element.

In a development, the device includes a second carrier element, in which the coaxial coupling conductor element is formed.

In a further development, the second carrier element is made of metal and forms a second outer conductor of the coaxial coupling conductor element. The cross section of the second carrier element may be rectangular and a second inner conductor is arranged in a groove of the first carrier element.

One or more of the present embodiments provide a patient table with a coaxial arrangement as described above for the data signal transfer between parts moving in a translational manner.

DETAILED DESCRIPTION

Figure 1:
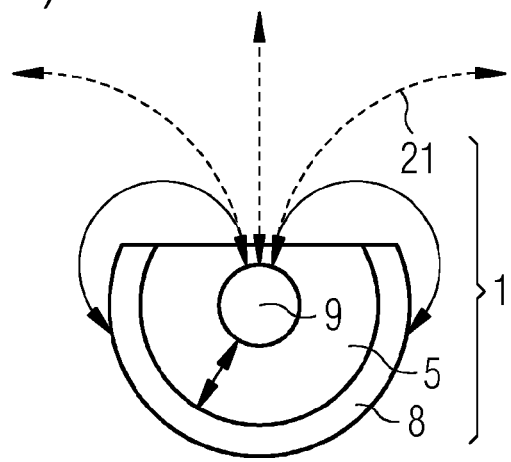
FIG. 1 shows a cross section through a coaxial conductor element.
Figure 1:
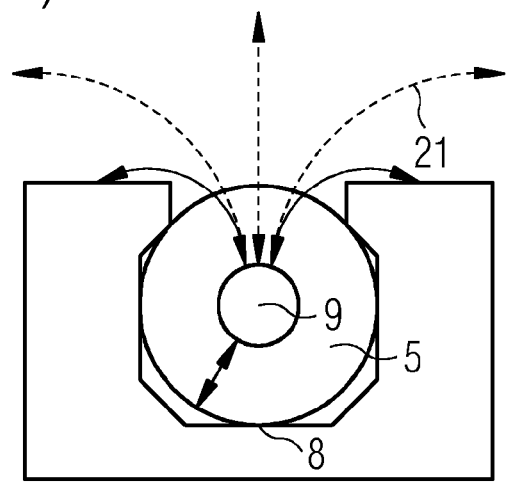

FIG. 1 shows cross sections through a longitudinally slit coaxial conductor element 1. The cross section A) shows a coaxial cable and the cross section B) shows a coaxial cable, in which the outer conductor was removed and which was inserted into a milled groove. The longitudinal slit may have a continuous or periodically spaced apart embodiment. The conductor element 1 includes a first inner conductor 9 and a first outer conductor 8. A dielectric 5, which fixes the first inner conductor 9 coaxially in relation to the first outer conductor 8, is situated between the first outer conductor 8 and the first inner conductor 9. The first outer conductor 8 is open toward the top, (e.g., slit open). An electric wave guided in the conductor element 1 may partially escape through the forming gap. The arising electric field is represented by field lines 21. In cross section B), the dielectric does not completely fill the milled groove.

Figure 2:
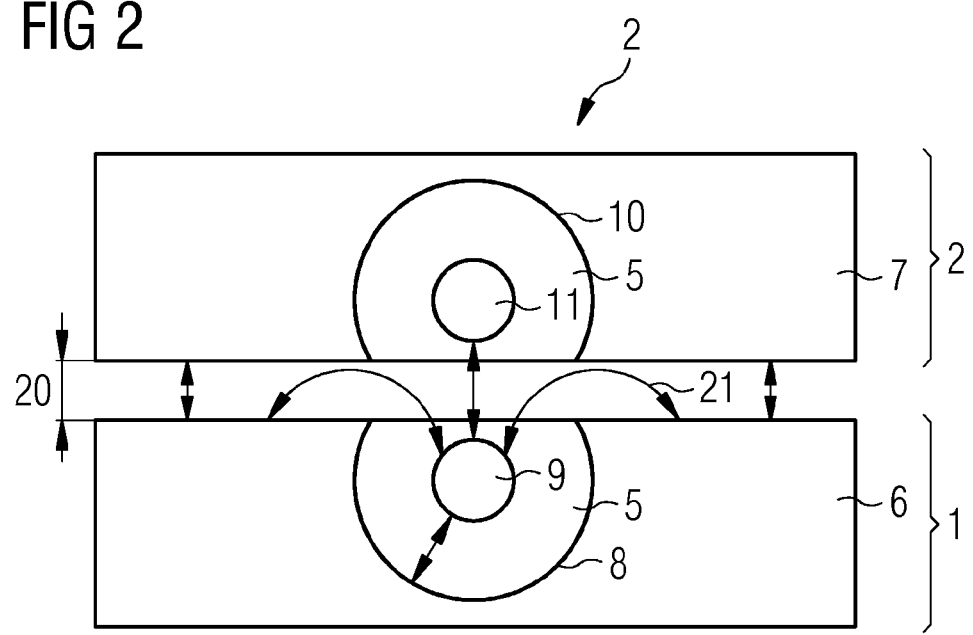
FIG. 2 shows a cross section through a device with a coaxial conductor element and a coaxial coupling conductor element.

FIG. 2 shows what happens if a longitudinally slit coaxial coupling conductor element 2 is brought into the near field of the slit coaxial conductor element 1. Electric energy from the near field couples into the coupling conductor element 2, which is, for example, also a coaxial cable. The electromagnetic field is represented by the field lines 21 thereof.

FIG. 2 shows a cross section through the conductor element 1 and the coupling conductor element 2 arranged at a distance therefrom by the air gap 20. The conductor element 1 includes an electrically conductive first carrier element 6 that forms the first outer conductor 8. The first inner conductor 9 with the dielectric 5 is pressed into the first carrier element 6. The coupling conductor element 2 includes an electrically conductive second carrier element 7 that forms the second outer conductor 10. The second inner conductor 11 with the dielectric 5 is pressed into the second carrier element 7. The air gap 20 is only a few millimeters wide.

The electrically conductive carrier elements 6 and 7 lying just over one another act in a capacitive manner and form a short circuit for high frequencies. Signal transfer is only possible between the first inner conductor 9 and the second inner conductor 11.

The electric conductor element 1 and electric coupling conductor element 2 have, for example, an external conductor 8, 10 diameter of approximately 5.5 mm and an internal conductor 9, 11 diameter of approximately 1.5 mm. By way of example, the carrier elements 6, 7 are made of copper, and the inner conductors 9, 11 are made of silver-coated copper. By way of example, the dielectric 5 is made of PTFE. Transfers with a carrier frequency up to 35 GHz are possible therewith. The coaxial cross section is to be reduced for higher frequencies in order to keep the coaxial conductor free from modes. As a result, there is also reduction in the possible spacing for the coupler structure.

Figure 3:
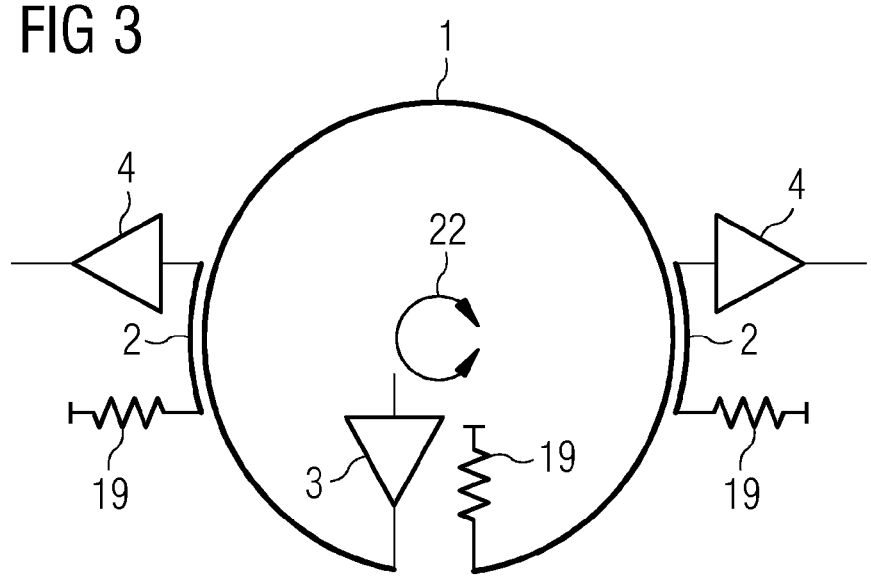
FIG. 3 shows a block diagram of a device with a rotatable coaxial conductor element.

FIG. 3 shows a block diagram of a device with a rotatable coaxial conductor element 1. A radiofrequency carrier signal modulated by the data signal is fed into the conductor element 1 at the first end thereof by the radiofrequency transmission unit 3. The conductor element 1 has an embodiment in accordance with FIG. 2 and is provided at the second end thereof with a termination 19 (e.g., a lossy line or a terminating resistance) for a reflection-free termination. The conductor element 1 is rotatably mounted in the direction of rotation 22.

Two coupling conductor elements 2, embodied in accordance with FIG. 2, are arranged opposite one another along the circumference of the conductor element 1 for the purposes of decoupling the radiofrequency carrier signal from the first conductor element 1. The coupling conductor element 2 may be a few wavelengths (e.g., a few cm) long and terminated by a termination 19 at the first end thereof. A radiofrequency reception unit 4 is connected at the second end thereof and receives and demodulates the decoupled radiofrequency carrier signal.

Optionally, the coupling conductor element 2 may be arranged in a rotatable manner, and the conductor element 1 may be arranged in a stationary manner.

Figure 4:
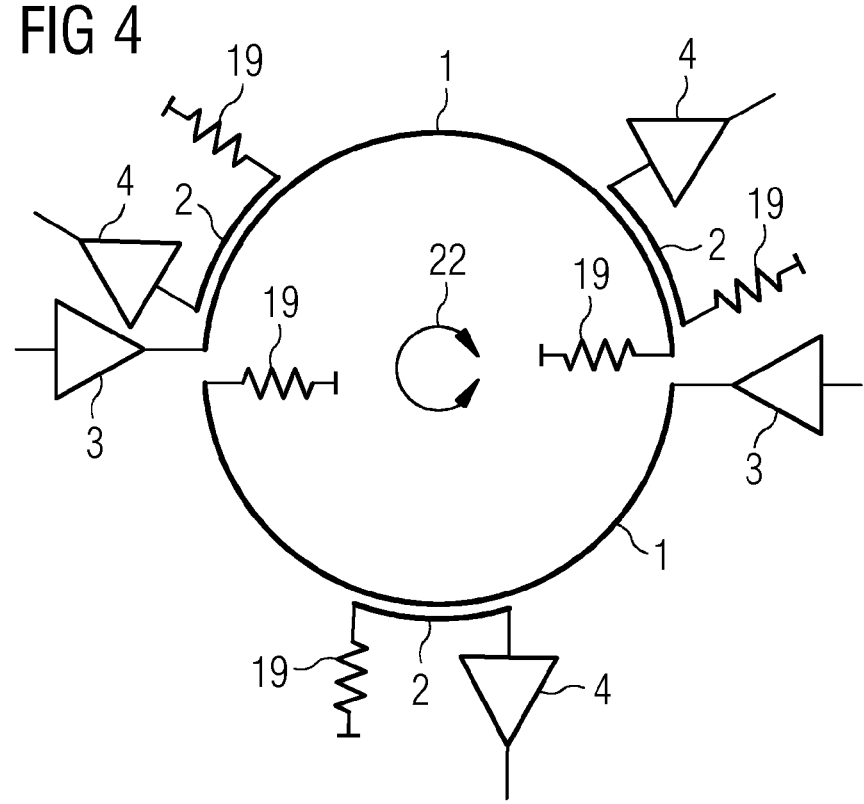
FIG. 4 shows a block diagram of a device with a rotatable segmented coaxial conductor element.

FIG. 4 shows a block diagram of a device with a rotatable coaxial conductor element 1 divided into two segments of equal length. A radiofrequency carrier signal modulated by the data signal is fed into both conductor elements 1 at the first ends thereof by the radiofrequency transmission unit 3. The conductor elements 1 are embodied in accordance with FIG. 2 and are provided at the second ends thereof with a termination 19 for a reflection-free termination. The conductor elements 1 are rotatably mounted in the direction of rotation 22.

One coupling conductor element 2, embodied in accordance with FIG. 2, is arranged along the circumference of the conductor elements 1 for the purposes of decoupling the radiofrequency carrier signal from the first conductor element 1. The coupling conductor element 2 may be a few wavelengths (e.g., a few cm) long and terminated by a termination 19 at the first end thereof. A radiofrequency reception unit 4 is connected at the second end thereof and receives and demodulates the decoupled radiofrequency carrier signal.

Optionally, the coupling conductor element 2 may be arranged in a rotatable manner, and the conductor element 1 may be arranged in a stationary manner.

Figure 5:
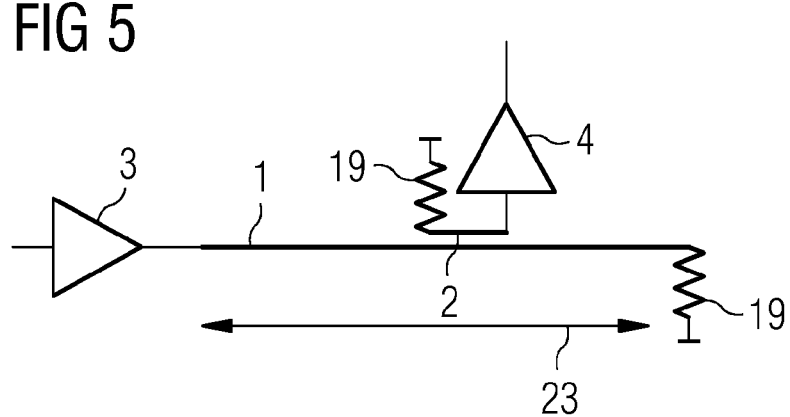
FIG. 5 shows a block diagram of a device with a coaxial conductor element displaceable in a translational manner.

FIG. 5 shows a block diagram of a device with a translationally displaceable coaxial conductor element 1. A radiofrequency carrier signal modulated by the data signal is fed into the conductor element 1 at the first end thereof by the radiofrequency transmission unit 3. The conductor element 1 has an embodiment in accordance with FIG. 2 and is provided at the second end thereof with a termination 19 for a reflection-free termination. The conductor element 1 is displaceably mounted in the direction of movement 23.

One coupling conductor element 2, embodied in accordance with FIG. 2, is arranged along the conductor element 1 for the purposes of decoupling the radiofrequency carrier signal from the first conductor element 1. The coupling conductor element 2 may be a few wavelengths (e.g., a few cm) long and terminated by a termination 19 at the first end thereof. A radiofrequency reception unit 4 is connected at the second end thereof and receives and demodulates the decoupled radiofrequency carrier signal.

Optionally, the coupling conductor element 2 may be arranged in a movable manner and the conductor element 1 may be arranged in a stationary manner.

Figure 6:
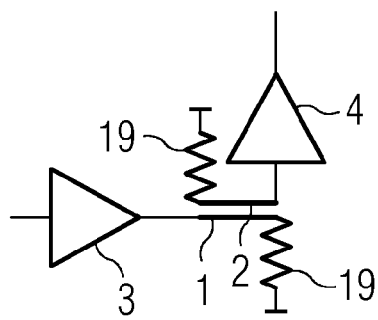
FIG. 6 shows a block diagram of a device with a stationary coaxial conductor element.

FIG. 6 shows a block diagram of a device with a stationary coaxial conductor element 1. A radiofrequency carrier signal modulated by the data signal is fed into the conductor element 1 at the first end thereof by the radiofrequency transmission unit 3. The conductor element 1 has an embodiment in accordance with FIG. 2 and is provided at the second end thereof with a termination 19 for a reflection-free termination.

One coupling conductor element 2, embodied in accordance with FIG. 2, is arranged along the conductor element 1 for the purposes of decoupling the radiofrequency carrier signal from the first conductor element 1. The coupling conductor element 2 may be a few wavelengths (e.g., a few cm) long and terminated by a termination 19 at the first end thereof. A radiofrequency reception unit 4 is connected at the second end thereof and receives and demodulates the decoupled radiofrequency carrier signal.

Figure 7:
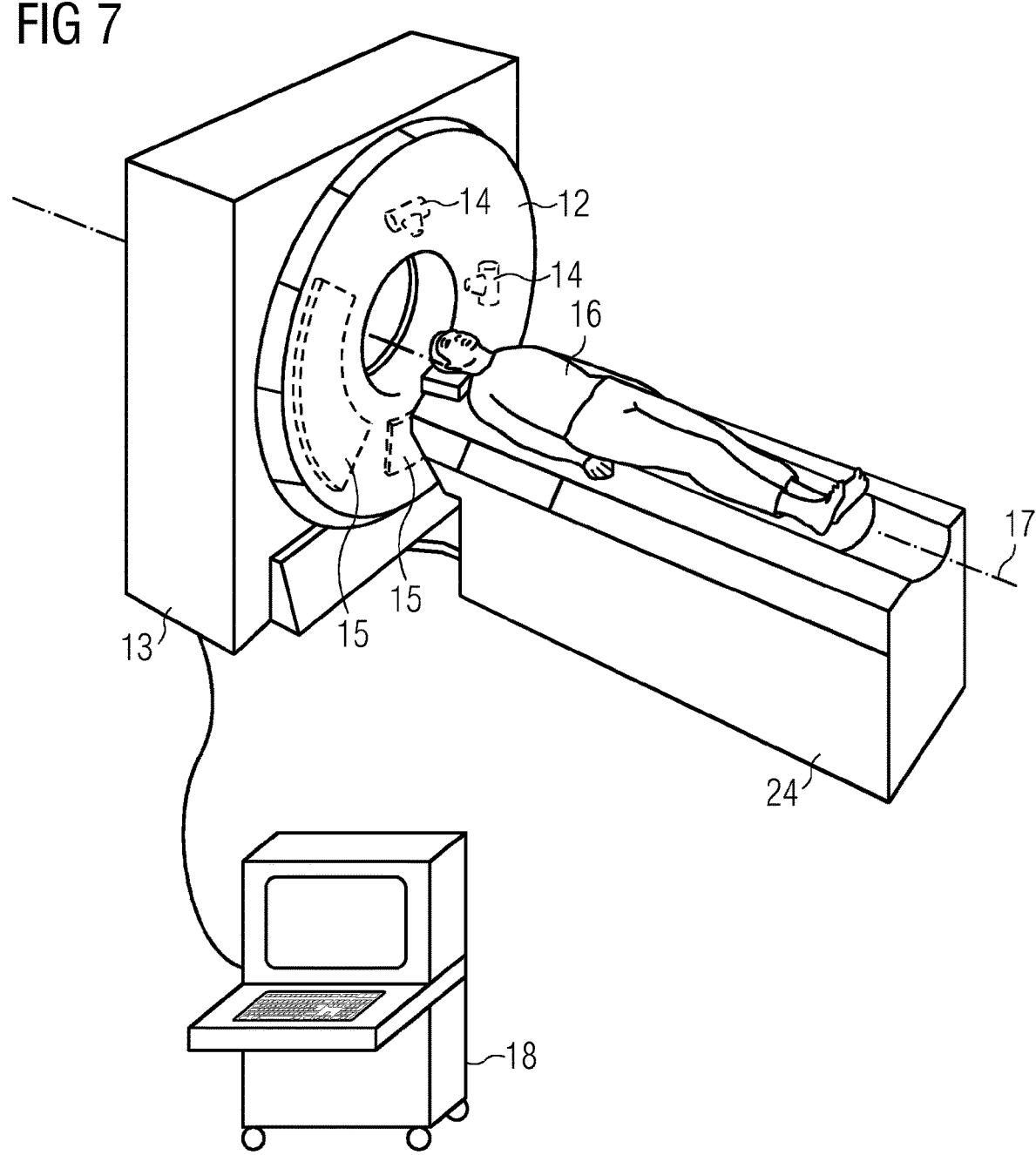
FIG. 7 shows one embodiment of a computed tomography system.

FIG. 7 shows a computed tomography system according to one or more of the present embodiments. The computed tomography system includes a stationary gantry part 13, in which a rotatable gantry part 12 is situated, with two x-ray tubes 14 and two x-ray detectors 15 being arranged thereon. For examination purposes, a patient 16 is introduced into a measurement field with the aid of a patient couch 20 that is displaceable along a system axis 17 such that an absorption of the x-ray radiation may be measured from different projection angles. A computer 18, which is configured as a control and computational unit, serves to control the system. Computer programs that carry out a control of the computed tomography system and an evaluation of the measured data, and also a reconstruction of the desired tomographic image data, are executed on the computer 18.

A large amount of arising data is to be transferred in a contactless manner (e.g., when transferring the detector data from the two detectors 15 on the rotatable gantry part 12(. A device according to one or more of the present embodiments in accordance with FIG. 1 to FIG. 4 for contactless transfer of electrical signals is attached to the rotatable gantry part 12 and the stationary gantry part 13 such that the signals may be transferred between the two gantry parts 12 and 13 that are rotatable in relation to one another.

Also, there may be a data transfer with a device according to FIG. 5 or FIG. 6 for the purposes of controlling patient tables in imaging medical engineering systems.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that ass equivalents and/or combinations of embodiments are intended to be included in this description.

LIST OF REFERENCE SIGNS

1 Coaxial conductor element
2 Coaxial coupling conductor element
3 Radiofrequency transmission unit
4 Radiofrequency reception unit
5 Dielectric
6 First carrier element
7 Second carrier element
8 First outer conductor
9 First inner conductor
10 Second outer conductor
11 Second inner conductor
12 Rotatable gantry part
13 Stationary gantry part
14 X-ray tube
15 X-ray detector
16 Patient
17 System axis
18 Computer
19 Termination
20 Air gap
21 Field lines
22 Direction of rotation
23 Movement direction
24 Patient couch

The invention claimed is:

1. A computed tomography system with a contactless data signal transfer, the computed tomography system comprising:
    at least one longitudinally slit coaxial conductor element having a reflection-free termination at a first end with a first resistance, wherein the at least one longitudinally slit coaxial conductor comprises an inner conductor and a dielectric disposed around the inner conductor, and wherein the at least one longitudinally slit coaxial conductor is arranged in a groove or comprises an outer conductor with a longitudinal slit;
    at least one radiofrequency transmission unit that feeds a radiofrequency carrier signal, modulated with a data signal to be transferred, into the at least one longitudinally slit coaxial conductor element at a second end;
    at least one longitudinally slit coaxial coupling conductor element that is terminated with a second resistance and configured to receive an emitted modulated radiofrequency carrier signal from a near field of the at least one longitudinally slit coaxial conductor element;
    at least one radiofrequency reception unit that is electrically connected to the at least one longitudinally slit coaxial coupling conductor element and is configured to extract the data signal from the received modulated radiofrequency carrier signal;
    a first gantry part arranged in a rotatable manner, the at least one longitudinally slit coaxial conductor element being arranged on the first gantry part in a circular-ring-shaped manner; and a second gantry part arranged in a stationary manner, the at least one longitudinally slit coaxial coupling conductor element being arranged on the second gantry part.

2. A computed tomography system with a contactless data signal transfer, the computed tomography system comprising:
- at least one longitudinally slit coaxial conductor element having a reflection-free termination at a first end with a first resistance, wherein the at least one longitudinally slit coaxial conductor comprises an inner conductor and a dielectric disposed around the inner conductor, and wherein the at least one longitudinally slit coaxial conductor is arranged in a groove or comprises an outer conductor with a longitudinal slit;
- at least one radiofrequency transmission unit that feeds a radiofrequency carrier signal, modulated with a data signal to be transferred, into the at least one longitudinally slit coaxial conductor element at a second end;
- at least one longitudinally slit coaxial coupling conductor element that is terminated with a second resistance and configured to receive an emitted modulated radiofrequency carrier signal from a near field of the at least one longitudinally slit coaxial conductor element;
- at least one radiofrequency reception unit that is electrically connected to the at least one longitudinally slit coaxial coupling conductor element and is configured to extract the data signal from the received modulated radiofrequency carrier signal;
- a first gantry part arranged in a rotatable manner, the at least one longitudinally slit coaxial coupling conductor element being arranged on the first gantry part; and
- a second gantry part arranged in a stationary manner, the at least one longitudinally slit coaxial conductor element arranged on the second gantry part in a circular-ring-shaped manner.

3. A patient table for imaging medical engineering systems with a contactless data signal transfer, the patient table comprising:
- at least one longitudinally slit coaxial conductor element;
- at least one radiofrequency transmission unit that feeds a radiofrequency carrier signal, modulated with a data signal to be transferred, into the at least one longitudinally slit coaxial conductor element;
- at least one longitudinally slit coaxial coupling conductor element that is configured to receive an emitted modulated radiofrequency carrier signal from a near field of the at least one longitudinally slit coaxial conductor element; and
- at least one radiofrequency reception unit that is electrically connected to the at least one longitudinally slit coaxial coupling conductor element and is configured to extract the data signal from the received modulated radiofrequency carrier signal,
- wherein the at least one longitudinally slit coaxial conductor element and the at least one longitudinally slit coaxial coupling conductor element are movably arranged relative to one another in a translational manner.

4. The computed tomography system of claim 1, wherein a frequency of the radiofrequency carrier signal is greater than 10 GHz.

5. The computed tomography system of claim 1, further comprising a first carrier element, in which the at least one longitudinally slit coaxial conductor element is formed.

6. The computed tomography system of claim 5, wherein the first carrier element is made of metal and forms the outer conductor of the at least one longitudinally slit coaxial conductor element.

7. The computed tomography system of claim 6, wherein the first carrier element has a rectangular cross section, and wherein the first carrier element comprises the groove.

8. The computed tomography system of claim 5, further comprising a second carrier element, in which the at least one longitudinally slit coaxial coupling conductor element is formed.

9. The computed tomography system of claim 8, wherein the second carrier element is made of metal and forms a second outer conductor of the at least one longitudinally slit coaxial coupling conductor element.

10. The computed tomography system of claim 9, wherein the second carrier element has a rectangular cross section, and the second inner conductor is arranged in a groove of the second carrier element.

11. The computed tomography system of claim 2, wherein a frequency of the radiofrequency carrier signal is greater than 10 GHz.

12. The computed tomography system of claim 2, further comprising a first carrier element, in which the at least one longitudinally slit coaxial conductor element is formed.

13. The computed tomography system of claim 12, wherein the first carrier element is made of metal and forms the outer conductor of the at least one longitudinally slit coaxial conductor element.

14. The computed tomography system of claim 13, wherein the first carrier element has a rectangular cross section, and
wherein the first carrier element comprises the groove.

15. The computed tomography system of claim 12, further comprising a second carrier element, in which the at least one longitudinally slit coaxial coupling conductor element is formed.

16. The patient table of claim 3, further comprising a first carrier element, in which the at least one longitudinally slit coaxial conductor element is formed.

17. The patient table of claim 16, wherein the first carrier element is made of metal and forms a first outer conductor of the at least one longitudinally slit coaxial conductor element.

18. The patient table of claim 17, wherein the first carrier element has a rectangular cross section, and a first inner conductor is arranged in a groove of the first carrier element.

19. The patient table of claim 16, further comprising a second carrier element, in which the at least one longitudinally slit coaxial coupling conductor element is formed.

20. The patient table of claim 19, wherein the second carrier element is made of metal and forms a second outer conductor of the at least one longitudinally slit coaxial coupling conductor element.

21. The computed tomography system of claim 1, wherein the longitudinally slit coaxial conductor element is a first longitudinally slit coaxial cable, and
wherein the longitudinally slit coaxial coupling conductor element is a second longitudinally slit coaxial cable.

22. The computed tomography system of claim 2, wherein the longitudinally slit coaxial conductor element is a first longitudinally slit coaxial cable, and
wherein the longitudinally slit coaxial coupling conductor element is a second longitudinally slit coaxial cable.

* * * * *